United States Patent [19]
Marchalonis et al.

[11] Patent Number: 5,911,990
[45] Date of Patent: Jun. 15, 1999

[54] T-CELL RECEPTOR PEPTIDES AND METHODS FOR PREVENTING THE PROGRESSION TO AIDS IN AN ANIMAL MODEL

[75] Inventors: John J. Marchalonis; Ronald R. Watson, both of Tucson, Ariz.; Keivan Dehghanpisheh, Portland, Oreg.; Yuejian Wang, St. Paul, Minn.; Dennis S. Huang, Shaker Heights, Ohio

[73] Assignee: Arizona Board of Regents on Behalf of the University of Arizona, Tucson, Ariz.

[21] Appl. No.: 08/696,049

[22] Filed: Aug. 13, 1996

[51] Int. Cl.$^6$ .......................... A61K 39/00; A61K 45/05; C07K 14/725

[52] U.S. Cl. ..................... 424/185.1; 424/278.1; 530/300; 530/395

[58] Field of Search ..................... 530/300, 350, 530/395, 868; 424/185.1, 207.1, 184.1, 278.1

[56] References Cited

PUBLICATIONS

Watson, R.R. 1989, Minireview of murine models for acquired immune deficiency syndrome. *Life Sci*, 44:iii.

Fauci, A.S. 1993, Multifactorial nature of human immunodeficiency virus disease: implications for therapy, *Science* 262:1011.

Selvey, L.A., H.C. Mose III, L.G. Graner, and R.J. Hodes, 1993. Preferential expansion and activation of Vβ5$^+$ CD4$^+$ T cells in murine acquired immunodeficiency syndrome. *J. Immunol*. 151:1712.

Soudeyns, H., N. Rebai, G.P. Pantaleo, C. Ciruli, T. Boghossian, P.P. Sekaly, and A.S. Fauci, 1993. The T cell receptor V beta repertoire in HIV–1 infection and disease, *Semin. Immunol*. 5:175.

Imberti, L., A. Sottini, A. Bettinaridi, M. Puoti, and D. Primi, 1991. Selective depletion in HIV infection of T cells that bear specific T cell receptor Vβ sequences. *Science* 254:860.

Bradley, W.G., N. Ogata, R.A. Good, and N.K. Day, 1993. Alteration of in vivo cytokine gene expression in mice infected with a molecular clone the defective MAIDS virus. *J. AIDS* 7:1.

Wang, Y., D.S. Huang, P.T. Giger, and R.R. Watson, 1993. The kinetics of imbalanced cytokine production by T cells and macrophages during the murine AIDS, *Adv. Biosci.* 86:335.

Gazzinelli, R.T., M. Makino, S.K. Chattopadhyay, C.M. Sanpper, A Sher, A.W. Hugin, and H.C. Morse III, 1992. Preferential activation of Th2 cells during progression of retrovirus–induced immunodeficiency in mice. *J. Immunol.* 148–182.

Kanagawa, O., B.A. Vaupel, S. Gayama, G. Koehler, and M. Kopf, 1993. Resistance of mice deficient in IL–4 to retrovirus–induced immunodeficiency syndrome (MAIDS). *Science* 262:240.

Wang, Y., S.K. Ardestani, B. Liang, L. Beckham, and R.R. Watson, 1994. Anti–IL–4 monoclonal antibody and interferon–γ administration retards development of immune dysfunction and cytokine dysregulation during murine AIDS. *Immunology* 83:384.

Marchalonis, J.J., H. Kaymaz, F. Dedeoglu, S.F. Schluter, D.E. Yocum, and A.B. Edmundson, 1992. Human autoantibodies reactive with synthetic autoantigens from T–cell receptor β chain. *Proc. Natl. Acad. Sci. USA* 89:332.

Toyonaga, B., and T.W. Mak, 1987. Genes of the T–cell antigen receptor in normal and malignant T–cells. *Annu. Rev. Immunol.* 5:585.

Marchalonis, J.J., H. Kaymaz, F. Dedeoglu, S.F. Schluter, and A.B. Edmundson, 1992. Antigenic mapping of a human light chain: correlation with 3–dimensional structure. *J. Protein Chem.* 11:129.

Feng, D.F., and R.F. Doolittle, 1987. Progressive sequence alignment as a prerequisite to correct phylogenetic trees. *J. Mol. Evol.* 25:351.

Wierda, W.G., D.S. Mehr, and Y.B. Kim, 1989. Comparison of fluorochrome–labeled and $^{51}$Cr–labeled targets for natural killer cytotoxicity assay. *J. Immunol. Methods* 122:15.

Watson, R.R., O.E. Odeleye, H.R. Darban, and M.C. Lopez, 1992. Modification of lymphoid subsets by chronic ethanol consumption in C57BL/6 mice infected with LP–BM5 murine leukemia virus. *Alcohol Alcoholism*27:417.

Lake, D.F., S.F. Schluter, E. Wang, R.M. Bernstein, A.B. Edmundson, and J.J. Marchalonis, 1994. Autoantibodies to the alpha/beta T–cell receptors in human immunodeficiency virus (HIV) infection: dysregulation and mimicry. *Proc. Natl. Acad. Sci. USA* 91:10849.

Boardette, D.N., R.H. Whitman, Y.K. Chou, W.J. Morrison, J. Atherton, C. Kenny, D. Liefeld, G.A. Hashim, H. Offner, and A.A. Vandenbark, 1994. Immunity to TCR peptides in multiple sclerosis, I. Successful immunization of patients with synthetic Vβ 5.1 and Vβ 6.1 CDR2 peptides, *J. Immunol.* 152:2510.

Odeleye, O.E., C.D. Eskelson, and R.R. Watson, 1992, Changes in hepatic lipid composition after infection by LP–BM5 causing murine AIDS. *Life Sci.* 51:129.

Mellors, J.W., B.P. Griffith, M.A. Ortiz, M.L. Landry, and J.L. Ryan, 1991. Tumor necrosis factor–alpha/cachectin enhances human immunodeficiency virus type 1 replication in primary macrophages. *J. Infect. Dis.* 163:78.

(List continued on next page.)

*Primary Examiner*—Thomas M. Cunningham
*Attorney, Agent, or Firm*—Arnold White & Durkee

[57] ABSTRACT

A novel peptide from the T-cell receptor is shown to be effective in preventing the progression to AIDS in an animal model. Methods for delaying the progression to AIDS and restoring normal immunological responses in an animal model following infection are shown and comprise administering through various systemic routes T-cell receptor peptide Vβ CDR1 to restore normal levels of Th1 cytokines interleukin 2 and interferon-γ, which are suppressed following infection, and those of Th2 derived cytokines interleukin 5, interleukin 6, interleukin 10, and immunoglobulin G, which are stimulated following infection.

6 Claims, No Drawings

PUBLICATIONS

Pantaleo, G., J.F. Demarest, H. Soudeyns, C. Graziosi, F. Denis, J.W. Adelsberger, P. Borrow, M.S. Saag, G.M. Shaw, R.P. Sekaly, and A.S. Fauci, 1994. Major expansion of CD8$^+$ T cells with predominant VB usage during the primary immune response to HIV. *Nature* 370–463.

Marchalonis, J.J., D.F. Lake, S.F. Schluter, K. Dehghanpisheh, R.R. Watson, N.M. Ampel, and J.N. Galgiani, 1995. Autoantibodies against peptide–defined epitopes of T–cell receptors in retrovirally infected humans and mice. In *Proceedings of the VIIIth International Symposium on Immunobiology of Proteins and Peptides*. Plenum Press, New York, in press.

Conrad B., Weissmahr, R.N., Arcari, R. Schupbach, J. and March, B. A human endogenous retroviral superantigen as candidate autoimmune gene in type I diabetes Cell 90(2):303–313, 1997.

Dehghanpisheh, K., Huang, D., Schluter, S.F., Watson, R.R. and Marchalonis, J.J. 1995. Production of IgG autoantibodies to T–cell receptors in mice infected with the retrovirus LP–BM5. Intl. Immunol. 7:31–36.

Indraccolo, S., Gunzberg, W.H., Leib–Mosch, C., Erfle, V. and Salmons, B. Identification of three human sequences with viral superantigen–specific primers. Mammalian Genome 6(5): 339–344, 1995.

Labrecque, N., McGrath, H., Subramanyam, M., Huber, B.T. and Sekaly, R.P. Human T Cells respond to mouse mammary tumor virus–encoded superantigen Vβ restriction and conserved evolutionary features. J. Exp. Med. 177(6):1735–1743, 1993.

Silverman, G.J. Pires, R. and Bouvet, J.P. An endogenous sialoprotein and a bacterial B cell superantigen compete in their $V_H$ family specific binding interactions with human Igs. J. Immunol. 157(10); 4496–4502, 1996.

Akolkar, P.N., Chirmule, N., Gulwani–Akolkar, B., Pahwa, S., Kalyanaraman, V.S., Pergolizzi, R., Macphail, S., and Silver, J. Vβ specific activation of T cells by the HIV glycoprotein gp 160. Scand. J. Immunol. 41(5):487–498, 1995.

Chen, Y–Z., Matsushita, S. and Nishimura, Y. Response of a human T–cell clone to a large panel of altered peptide ligands carrying single residue substitutions in an antigenic peptide. J. Immunol. 157:3783–3790. 1996.

Hodara, V.L., Jeddi–Tehrani, M., Grunewald, J., Andersson, R., Scarlatti, G., Esin, S., Holmberg, V., Libonatti, O. and Wigzell, H. HIV infection lead to differential expression of T–cell receptor Vβ genes in CD4+ and CD8+ T cells. AIDS 7(5):633–638, 1993.

Jason, J., Inger, K.L. and Orloff, S.L. HIV antigens and T–cell receptor variable β chain families. Scand. J. Immunol. 45:81–90, 1997.

Johnson, H.M., Torres, B.A. and Soos, J.M. Superantigens; structure and relevance to human disease. Proc. Soc. Exp. Biol. Med. 212(2):99–109, 1996.

Kotzin, B.L., Leung, D.Y., Kappler, J. and Marrack, P. Superantigens and their potential role in human disease. Adv. in Immunol. 54:99–166, 1993.

Trentin, L. Zambello, R., Facco, M., Sancetta, R., Cerutti, A. Milani, A. Tassinari, C., Crivellaro, C., Ciprani, A., Agostini, C., and Semenzato, G. Skewing of the T–cell receptor repertoire in the lung of patients with HIV–1 infection. AIDS 10(7):729–737, 1996.

Utz, U., Banks, D., Jacobson, S. and Biddison, W.E. Analysis of the T–cell receptor repertoire of Human T–cell leukemia virus type 1 (HTLV–1) Tax–specific CD8+ cytotoxic T lymphocytes from patients with HTLV–1 associated disease: evidence for oligoclonal expansion. J. Virol. 70(2):843–851, 1995.

Vandenbark, A.A., Chou, Y.K., Whitham, R., Mass, M. Buenafe, A., Liefeld, D., Kavanagh, D., Cooper, S., Hashim, G.A., and Offner, H. Treatment of multiple sclerosis with T–cell receptor peptides: results of a double–blind pilot trial. Nature Medicine 2(10):1109–1115, 1996.

Watson, R.R., Dehghanpisheh, Huang, D.S., Wood, S., Ardestani, S.K., Laing, B., Marchalonis, J.J. and Wang, Y. 1995, T–cell receptor vβ CDR1 peptide administration moderates immune dysfunction and cytokine dysregulation induced by murine retrovirus infection. J. Immunol. 155:2282–2291, 1995.

Watson, R., et al., "T Cell Receptor Vβ Complementarity–Determining Region 1 Peptide Administration Moderates Immune Dysfunction and Cytokine Dysregulation Induced by Murine Retrovirus Infection", *The Journal of Immunology* 1995, 155: 2282–2291.

Liang, B., et al., "T–Cell–Receptor Dose and the Time of Treatment During Murine Retrovirus Infection for Maintenance of Immune Function", *Immunology* 1996, 87: 198–204.

Dehghanpisheh, K., et al., "Production of IGG autoantibodies to T–Cell Receptors in Mice Infected with the Retrovirus LP–BM5", Int. Immunol. 1995, 7: 31.

Marchalonis J.J. et al., "Autoantibodies Against Peptide–Defined Epitopes of T–Cell Receptors in Retrovirually Infected Humans and Mice", (*Immunobiology of Proteins and Peptides VIII* 1995) Adv. Exp. Med. Biol. 383:211–222.

Marchalonis J.J. et al., "Autoantibodies to T–Cell Receptors Following Infection by Murine Retrovirus", *Lymphology* 1994, 27S:853.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 16 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:1:

Cys Lys Pro Ile Ser Gly His Asn Ser Leu Phe Trp Tyr Arg Gln Thr
   1               5                   10                  15

(2) INFORMATION FOR SEQ ID NO:2:

(i) SEQUENCE CHARACTERISTICS:
       (A) LENGTH: 16 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:2:

Thr Gly Thr Ser Ser Asp Val Gly Gly Tyr Asn Tyr Val Ser Trp Tyr
   1               5                   10                  15

T-CELL RECEPTOR PEPTIDES AND METHODS FOR PREVENTING THE PROGRESSION TO AIDS IN AN ANIMAL MODEL

The U.S. Government has paid-up license in this invention and the right in limited circumstances to require the patent owner to license others on reasonable terms as provided for by the terms of Grant Nos. AA-08037 and CA-42049 awarded by the National Institute of Health.

FIELD OF THE INVENTION

The present invention relates generally to a novel treatment for use in preventing the progression to AIDS in an animal model. Unlike most present efforts now being made to treat HIV and AIDS with antiviral drugs, and the push to develop new antiviral drugs that are effective for treating AIDS, the present invention relates to the novel use of a peptide derived from human T-cell receptors.

BACKGROUND OF THE INVENTION

Acquired immune deficiency syndrome (AIDS) is a disease of retroviral etiology, characterized by immune dysfunction, opportunistic infections, and eventually death. Murine acquired immune deficiency syndrome (MAIDS), induced by infection with the murine LP-BM5 leukemia retrovirus (MuLV) mixture, causes a progressive and profound immunodeficiency. It is strikingly similar to human AIDS, with splenomegaly, lymphadenopathy, and hypergammaglobulinemia in the early stage of retrovirus infection, progressive defects in T and B cell function, and reduction of host resistance to pathogens and neoplasia. These similarities exist even though human immunodeficiency virus (HIV), a lentivirus, and the retrovirus causing murine AIDS, MuLV, a C-type retrovirus, represent different types of retroviruses (1).

The immunopathogenic mechanisms underlying HI V infection and disease are not unidimensional; they are extremely complex (2). Preferential expansion, deletion, and activation of some CD4$^+$ αβ T cells induced by retroviral super or chronic antigen (Ag) exposure in human and murine AIDS may be important immunopathogenic mechanisms (3–5). Selective Ag activation of CD4$^+$ αβ T cells may lead to polyclonal stimulation of T and B cells at early stages, with subsequent aberrant cytokine production CD4$^+$ T cell depletion. Eventually, these abnormalities lead to profound immunosuppression of cell-mediated immunity and immunodeficiency (2).

The aberrant cytokine production due to retrovirus infection, caused by a switch from T helper 1 (Th1) response to T helper 2 (Th2) response, promotes the progression to AIDS (6). In HIV$^+$/AIDS patients and MuLV-infected mice, T cell proliferation and Th1 cytokine (interleukin-2 (IL-2) and interferon-γ) production decline, while Th2 cytokine (IL-4, IL-5, IL-6, and IL-10), and Ig production increase (7–10). The Th1 to Th2 conversion may determine the fatal outcome of the disease as part of the mechanism producing severe immunodeficiency and loss of disease resistance during the progression to AIDS. When IL-4-deficient mice (IL-4 gene knockout) that are defective in Th2 cytokine responses are infected with LP-BM5 retrovirus, there is no lethality, and the development of T cell abnormalities associated with murine retrovirus infection is delayed (11). Administration of anti-IL-4 monoclonal antibody (Mab) to LP-BM5 retrovirus-infected mice or restoring the Th1 cytokine, IFN, by injection also normalizes the imbalance of Th1 and Th2 responses induced by retrovirus infection, prevents retrovirus-induced suppression of immune responses, and alleviates the typical murine AIDS symptoms: splenomegaly and hypergammaglobulinemia (12).

Autoantibodies (AAb) binding a peptide determinant corresponding to the first complementarity determining region (CDR1) of the T-cell receptor (TCR) Vβ domain were elevated early in murine retrovirus infection (13). Elevation of the levels of these AAbs is an early event following retroviral infection that corresponds in part to the general polyclonal activation of B cells with selectivity for particular Vβ sequences that occurs later. The production of high levels of anti-TCR AAb early in this disease with continued production of some AAbs suggests that they might be involved in retrovirus immunopathogenesis. The AAb directed against CDR1 determinants can be considered natural Ab against public or regulatory idiotypes (Id) (14), since this region is the least variable of the CDR and is completely specified by the Vβ gene sequence.

Preferential expansion of some TCR αβ CD4$^+$ T cells induced by retroviral superantigens in both human and murine retrovirus infection is an important immunopathogenic mechanism (2, 5). Selective expansion/deletion of some TCR αβ CD4$^+$ T cells may lead to polyclonal activation of T and B cells at an early stage, and subsequent aberrant cytokine production. Eventually these abnormalities lead to profound immunodeficiency with immunosuppression of cell-mediated immunity.

SUMMARY OF THE INVENTION

The present invention provides a T-cell receptor (TCR) peptide which, when administered to a host infected with an immunodeficiency-type retrovirus, is effective in preventing the progression to AIDS. The present invention also provides methods for preventing the progression to AIDS in an infected host, comprising administering TCR Vβ CDR1 peptide to an infected host by various systemic routes, thus arresting the development of the immune dysfunction and cytokine dysregulation which allow retrovirus infections to weaken the host facilitating life-threatening pathogens.

DETAILED DESCRIPTION OF THE PREFERRED EMBODIMENTS

In the present invention, administering a peptide corresponding to the first complementarity determining region of the T-cell receptor Vβ domain (TCR Vβ CDR1) and having the sequence Cys Lys Pro Ile Ser Gly His Asn Ser Leu Phe Trp Tyr Arg Gln Thr (SEQ ID NO:1) to a host infected with an immunodeficiency-type retrovirus prevents retrovirus-induced suppression of immune responses and normalizes cytokine production. The TCR Vβ CDR1 peptide, a synthetic molecule, was obtained under contract from various suppliers, including the Department of Biochemistry and Molecular Biology at the Medical University of South Carolina, Charleston, and the University of Arizona Biotechnology Center, Tucson. The peptide was synthesized using Applied Biosystems Peptide Synthesizers, and the purity was determined by amino acid composition and sequence analysis. When necessary, peptides were purified by high performance liquid chromatography (HPLC) under reverse phase conditions. The average purity of the peptide prior to purification by HPLC was 90%.

The present invention provides methods of delaying the onset of AIDS, comprising administering by various systemic routes TCR Vβ CDR1 peptide to a host infected with an immunodeficiency-type retrovirus in order to restore normal levels of Th1 cytokines, such as interleukin 2 and interferon-γ, and Th2 derived cytokines, such as interleukin 5, interleukin 6, interleukin 10, and immunoglobulin G. The present invention also provides methods for reversing the deleterious effects of infection with an immunodeficiency-type retrovirus, comprising administering TCR Vβ CDR1 peptide to a host infected with said immunodeficiency-type retrovirus, to restore normal levels of Th1 cytokines, such as interleukin 2 and interferon-γ, and Th2 derived cytokines, such as interleukin 5, interleukin 6, interleukin 10, and immunoglobulin G.

In addition, the present invention provides methods for modulating the immune response in a mammal infected with an immunodeficiency-type retrovirus, comprising administering by various systemic routes an amount of TCR Vβ CDR1 peptide sufficient to restore normal levels of Th1 cytokines and Th2 derived cytokines. Methods of suppressing progression to immune dysfunction and cytokine dysregulation caused by HIV infection, comprising administering TCR Vβ CDR1 peptide in an amount sufficient to restore normal levels of Th1 cytokines and Th2 derived cytokines, are also shown.

Moreover, methods of preventing immunosuppression and cytokine dysregulation induced by infection with an immunodeficiency-type retrovirus, comprising administering systemically to an infected host TCR Vβ CDR1 peptide in an amount sufficient to restore normal immunological functions, are shown. Methods are also shown for altering the immune system response of a host infected with an immunodeficiency-type retrovirus, comprising artificially introducing a TCR Vβ CDR1 peptide into the bloodstream or immune system by injection so as to artificially stimulate the immune system to restore normal levels of Th1 cytokines and Th2 derived cytokines.

Systemic routes that may be used for administering the TCR Vβ CDR1 peptide in all embodiments of the present invention include intravenous injection, intraperitoneal injection, oral administration, subcutaneous administration, intramuscular administration, and administration by autologous dendritic cells. Oral administration usually leads to tolerance, whereas the other systemic routes lead to distinct types of immunity that may be particularly useful in certain infections or disease states. The peptide may be administered with or without adjuvant such as alum, Freunds complete or incomplete adjuvants, poly (AU) or RIBI adjuvant, or coupled to a carrier such as albumin, ovalbumin, or other native or engineered proteins.

Typically, doses of 5 mg/kg of body weight to 25 mg/kg of body weight of TCR Vβ CDR1 peptide in saline are administered in divided doses following infection. Preferably, doses of approximately 10 mg/kg of body weight to 25 mg/kg of body weight of TCR Vβ CDR1 peptide in saline are administered in divided doses. Most preferably, doses of 10 mg/kg of body weight are administered. Multiple doses administered approximately once per month increase the efficacy of the TCR Vβ CDR1 peptide therapy. Dosage amounts, however, may vary depending on the route of administration and depending on whether the TCR Vβ CDR1 peptide is administered with or without adjuvant.

The theory underlying the TCR Vβ CDR1 peptide administration approach is that it should be beneficial in any situation, whether it be infectious, autoimmune, or environmental, in which autoantibodies against the family of TCR Vβ CDR1 peptides are generated. This includes infection with C-type retroviruses MULV/MAIDS), lentiviruses (HIV including HIV-1, HIV-2, and HIV-3, simian immunodeficiency virus (SIV), and feline immunodeficiency virus (FIV)), infection with non-viral pathogens (e.g. coccidiomycosis), and contact with environmental agents such as oils and adjuvants that amplify various features of the immune system. In all embodiments of the present invention, infections by immunodeficiency-type retroviruses that may be challenged by administering TCR Vβ CDR1 peptide include C-type retroviruses and lentiviruses. The changes in retrovirus-induced immune dysfunction and cytokine production in the infected host following administration of the TCR Vβ CDR1 peptide occur simultaneously with restoration of tissue vitamin E, a mild immunostimulant and reduced lipid peroxidation in tissues, which decreases the oxidative stress caused by free radical products, i.e., lipid fluorescence and diene conjugates.

Most antigens (Ag) are recognized through their interaction with the variable (V) portions of the TCR α- and β-chains. However, T cells recognize another category of ligands, the superantigens, on the basis of the expressed Vβ region alone, independently from the other variable TCR segments. The progression of CD4$^+$ T cell expansion/depletion requires stimulation of T cell clones or subgroups with retroviral chronic or superantigen exposure, resulting over time in excessive activation followed by energy of CD4$^+$ T cells bearing Ag-selected Vβ. AAb against peptide-defined epitopes of TCR that were used to select the peptide for administration studies here were also found in high levels in HIV$^+$ patients (12). This overproduction may result from a failure in regulation.

Two potential mechanisms may be responsible for prevention of immune dysfunction during immunodeficiency-type retrovirus infection and concomitant TCR Vβ CDR1 peptide administration: (1) immunization against specific regulatory determinants on the products of individual Vβ genes, and (2) the possibility that peptides corresponding to the CDR1 and Fr2 segment of the Vβ-chain could interact with MHC molecules necessary for the presentation of peptide Ag, altering this process (24). A general mechanism of this nature is required because the effective peptide corresponds to only one of a possible set of >30 peptides, and it is unlikely that any single one would have an overall regulating effect based upon its individual ID specificity. However, immunological cross-reactivity between the TCR Vβ CDR1 peptide and other CDR1 sequences is expected because 51% of 51 major human TCR Vβ gene family sequences show at least 50% identity to the TCR Vβ CDR1 peptide. Both affinity purified naturally occurring human autoantibodies and monoclonal hybridomas expressing naturally occurring human and murine autoantibodies to the TCR Vβ CDR1 peptide can cross-react with between 2 and 7 other CDR1 peptides out of a test set of 24 individual human Vβ gene products, thus indicating cross-reactivity. The full 16 residue length is required for binding of the autoantibodies (Marchalonis, unpublished) as well as for the correction of the immunological defects induced by retroviral infection (34).

AAb to TCR Vβ induced by administration of TCR Vβ CDR1 peptide may slow the selective deletion/expansion of some Vβ T cells by cytolysis or other inhibitory mechanisms, including obstructed binding of the Ag to TCR Vβ-chains. The increased production of AAb to the TCR Vβ CDR1 peptide alone during AIDS may not be sufficient to alter the TCR Vβ expression profiles induced by retroviral super or chronic Ag exposure. Retrovirus infection induced selective induction of high levels of AAb against the TCR Vβ CDR1 peptide, presumably due to increased TCR Vβ T cell expression. The prevention of retrovirus-induced immunosuppression and cytokine dysregulation by TCR Vβ CDR1 peptide administration may be due to a difference in the affinities of the different Vβ for the superantigen after specific AAb interference.

Patients infected with HIV display a progressive loss of $CD4^+$ Th cell function, often taking years before cell numbers and other cell functions are depressed sufficiently to produce AIDS (37). The loss of resistance to HIV infection and/or progression to AIDS may be dependent on a switch from Th1- to Th2-subset dominated responses (9). Progression to AIDS is characterized by decrease in Th1-cytokine (IL-2 and IFN-γ) production concomitant with an increase in Th2-cytokine (IL-6 and IL-10) production. Th1 and Th2 cytokine profiles in retrovirus-infected mice are in accordance with this hypothesis (14, 15). Similarly, progression to severe pathology due to murine retrovirus infection is characterized by loss of Th1 cytokine (IL-2 and IFN-γ) production concomitant with increases in Th2 cytokine (EL-5 and IL-10) production (9, 14, 15). Th1 and Th2 cytokine profiles in murine retrovirus infection are in accordance with this hypotheses.

The presence of a dose-response relationship as well as significant immune preservation in the presence of low doses of peptide in combination with two adjuvants further suggests an immunoregulatory mechanism. TCR Vβ CDR1 peptide administration before or early in the infection could slow activation of T cells, as we found a smaller increase in $IL-2R^+$ activated cells in immunized infected animals than in the infected unimmunized mice. Thus, during TCR Vβ CDR1 peptide administration, fewer cells may be activated to become Th2 or permitted to remain as immature Th0 cells with their high production of IL-4 and IL-10. This would preserve, but not restore, normal function in most bystander cells that were close enough to be affected by cytokines produced by T cell clones stimulated by super or chronic retroviral Ag exposure without the increased IL-4 production by Th2 cells. In this situation, more cells would remain as Th1 cells, producing IFN-γ and IL-2 during retrovirus Ag exposure. They would also suppress Th2 cytokine production in neighboring cells.

Recent studies have demonstrated in C57B1/6 mice that the stimulation of a strong Th1 immune response via *Leishmania major* infection before the onset of or early in the progression of LP-BM5 infection inhibits the development of murine AIDS symptoms (27). Administration of TCR Vβ CDR1 peptide both before and after infection significantly prevents the murine retrovirus-induced suppression of IL-2 and IFN-γ secretion, while the control peptide, MCG3, from the λ L chain V region of Ig may not. IL-2 is an important growth factor for T cells, and its increased release after TCR Vβ CDR1 administration is in accordance with restored T cell proliferation, as is the loss of IL-2 secretion by cells from mice progressing to severe pathology during murine retrovirus infection (14, 15). IFN-γ has multiple distinct biologic activities, including antiviral activity, activating phagocytosis of macrophages and neutrophil cells, and stimulation of cytotoxicity by NK cells and cytotoxic T lymphocytes (CTL) (28). Thus, increased IFN-γ caused by TCR Vβ CDR1 peptide prevents the development of suppressed cell-mediated immunity in murine AIDS. Increased production of IFN-γ by TCR Vβ CDR1 peptide is also in agreement with the enhancement of NK cell activity by the peptide.

However, IFN-γ inhibits Th2 cytokine secretion, which usually is elevated during the progression of the retrovirus infection. This is supported by our findings that administration of TCR Vβ CDR1 peptide in murine AIDS significantly reduces retrovirus-induced elevation of IL-5, IL-6, and IL-10 production and IgG production, while a control peptide does not. Increased production of IFN-γ by TCR Vβ CDR1 peptide administration after retrovirus infection is also in agreement with the enhancement of NK cell activity by the peptide. Taken together, the prevention of imbalanced Th1 and Th2 cytokine production by TCR Vβ CDR1 peptide administration contributes to the normalization of the entire immune response, thereby retarding the development of immune dysfunction during murine retrovirus infection. These findings are also supported by increased $CD8^+$ with selected Vβs (31) and AAb to HIV (32), which react with some Vβs. The dose of peptide that produces optimal slowing of development of immune dysfunction during murine retrovirus infection (200 μg/mouse or approximately 10 mg/kg of body weight) is the same dose found to be optimal in humans with an autoimmune disease (26). The two adjuvants tested enhanced the effectiveness of low doses of a TCR Vβ peptide. Thus, immunization may be involved with the production of AAb (24) or cellular immunity.

In vivo activated B cells and macrophages from HIV patients produce high levels of IL-6 and TNF-α (2), as do LPS-stimulated splenocytes and peritoneal macrophages for LP-BM5 retrovirus-infected mice (14). An elevated level of TNF-α may be involved with lipid metabolism, inducing hypertriglyceridemia (28) and loss of vitamin E (29) and increased lipid peroxidation (28) during the development of murine AIDS. Elevated levels of TNF-α have also been associated with the stimulation of HIV replication in macrophages/monocytes and T cells (30). Thus, reduction of elevated levels of TNF-α in murine retrovirus infection by TCR Vβ CDR1 peptide administration ameliorates pathologic symptoms of the host induced by retrovirus infection. Peptide administration also largely prevented the loss of tissue vitamin E (R. R. Watson and B. Liang, unpublished observations).

Increased IL-6 production may explain the hyper-γ-globulinemia and global B-cell dysfunction seen with both pathogens (40). IFN, vitamin E and their combined administration significantly normalized the increased production of IL-6 by LPS-stimulated splenocytes from retrovirus-infected mice. As IL-6 and other Th2 cytokines are required to maintain hyper-γ-globulinemia and global B-cell dysfunction of murine AIDS, their reduced production, or altered restoration of IFN or vitamin E, would prevent excessive B-cell activity, including eventual B-cell lymphoma. IL-6 also governs the production of acute-phase reactants by hepatocytes and their tissue damages (28). Elevated levels of IL-6 have been associated with the stimulation of HIV replication in macrophages and T cells (30, 41). Thus, normalization of elevated levels of IL-6 by IFN and vitamin E should ameliorate pathological symptoms initiated by the murine retrovirus, explaining the partial normalization of spleen weight.

Peptide administration did not significantly prevent lymphadenopathy and splenomegaly, although there was a tendency toward less pronounced splenomegaly in specifically treated animals. Thus, TCR Vβ CDR1 peptide treatment may not ameliorate all symptoms following from retrovirus infection in the murine AIDS (MAIDS) model, such as prevention of deaths from asphyxiation by enlarged lymph nodes. However, conclusive observations may not yet be apparent in this case, given the statistical error in measurement of spleen size.

In addition, administration of a single Vβ TCR peptide did not totally prevent immune dysfunction. AAbs were maintained in high levels to two of seven Vβ peptide families tested (24), suggesting that several T cell families or clones were stimulated by the retrovirus infection. Deletion of some Vβ genes significantly delayed arthritis onset (33). This suggests that the prevention of immune dysfunction by peptide administration in retrovirus-induced immunodeficiency syndrome (MAIDS) may be due to modulation of a T cell subset. As the spleen weight and lymph node size were not significantly reduced, we would still expect deaths due to asphyxiation, with enlarged lymph nodes, while maintaining near normal infectious disease resistance. Complete maintenance of normal immune function may be possible by preventing stimulation of all clones induced by the murine retrovirus Ag by administration of the Vβ peptides from the several TCR clones stimulated by murine retrovirus infection.

In experiments with the murine MAIDS model, administration of TCR Vβ CDR1 in saline by intraperitoneal injection either before (prophylaxis) or after (therapeutic) infection with the LP-BM5 MuLV retrovirus modulates retrovirus-induced immune dysfunction and cytokine dysregulation of T-cell function. In the prophylactic model, TCR Vβ CDR1 peptide was administered twice, on days −7 and −3 before retrovirus infection. In the therapeutic model, the mice were administered peptide on days 10 and 14 post-infection. Doses of peptide ranging from 0 to 500 μg/mouse were administered, in the presence or absence of adjuvants such as poly (AU) or RIBI adjuvant. An effective dose in both cases was 200 μg/mouse administered intraperitoneally in saline, although the addition of adjuvant enabled the use of less peptide in certain cases. For example, doses of 5 and 25 μg/mouse administered in the presence of adjuvant improved both the capacity for B and T cell mitogenesis in retrovirally infected mice.

The preferred dose of 200 μg/mouse in saline administered by intraperitoneal injection corresponds to approximately 10 mg/kg of body weight as a preferred dosage to be extrapolated for human usage, given that the body weight of a mouse is approximately 20 g. Dosage amounts, however, may vary depending on the route of administration and depending on whether the TCR Vβ CDR1 peptide is administered with or without adjuvant. For example, for subcutaneous administration by injection, less than 1 mg/kg of body weight may be administered for the peptide therapy to be effective. Preferably, peptide administered to a host infected with an immunodeficiency-type retrovirus should be made in at least two administrations, and multiple doses administered approximately once per month may increase efficacy.

Administration early or with a significant amount of TCR Vβ CDR1 peptide may be necessary to prevent immune dysfunction, and administration early in the infection, prior to significant immune dysfunction, may be critical. When administered shortly after LP-BM5 infection, the TCR Vβ CDR1 peptide largely, but not totally, maintains normal cytokine production. Preservation of immune function occurs similarly in mice that are administered the peptide before as well as after retrovirus infection. The greater the elapsed time post-infection before peptide administration, the greater the immune dysfunction that develops. Thus, TCR Vβ CDR1 peptide administration prevents immune dysfunction rather than restores it. However, a control peptide from a λ L chain CDR1 has no effect on preventing retrovirus-induced immune deficiency. The addition of adjuvant has a variable effect expanding the efficacy of very low (otherwise ineffective) doses of TCR antigen. TCR Vβ CDR1 peptide functions as an immunoregulatory element in the complex networks of interactions among the components of the immune system and anti-oxidation system.

In the murine model, the concentrations of hepatic and cardiac vitamin E are significantly ($P<0.05$) reduced by retrovirus infection (36), while TCR Vβ CDR1 peptide administration, at dosages of about 200 μg/mouse and 4-weeks postinfection, significantly ($P<0.05$) maintains hepatic and cardiac vitamin E levels at or near those of uninfected mice (36). Retrovirus infection significantly ($P<0.05$) increases hepatic and cardiac lipid peroxidation that produces more free radical products, i.e., lipid fluorescence and diene conjugates (36). TCR Vβ CDR1 peptide administration, at dosages of 100–500 μg/mouse and 4-weeks postinfection, significantly ($P<0.05$) reduces the hepatic and cardiac-free radical products (36).

The study of TCR Vβ CDR1 peptide provides an insight into the pathogenesis during progression to AIDS, as well as into the mechanisms of idiotypic networks involving AAb and autoreactive T cells as regulatory elements. These results also expand understanding of the roles of vitamin E and free radical products on regulation of immune function during retrovirus infection, which support the concept that combination of immune therapy and vitamin E supplementation therapy for murine retrovirus infection may be more efficacious than either alone.

In summary, a TCR Vβ CDR1 peptide is a potentially immunomodulating agent that achieves its immune system-enhancing effects through indirect mechanisms, possibly by preventing selective expansion of TCR Vβ T cells induced by the chronic retroviral Ag exposure. These findings help to evaluate the mechanisms contributing to retrovirus-induced immunodeficiency and to learn how to prevent their functioning. TCR Vβ CDR1 peptide administration may provide long term prevention of retrovirus-induced immune dysfunction. In addition, the use of TCR Vβ CDR1 peptide may be important in forestalling initial episodes of general immune disorders in some patients by extending the period between retrovirus infection and the appearance of immune deficiencies.

EXAMPLE 1
Animals and Murine AIDS

Female C57B1/6 mice, 5 wk old, were obtained from Charles River Laboratories (Wilmington, Del.). Animals were cared for as required by the University of Arizona Committee on Animal Research. After 2 wk in the animal facility at the Arizona Health Sciences Center, the mice were randomly assigned to one of the following six treatments: (1) uninfected normal mice injected with saline (pyrogen free); (2) uninfected normal mice injected with MCG3 (a synthetic peptide containing the CDR1 sequence of MCG-λ L chain) control peptide; (3) uninfected normal mice injected with TCR Vβ CDR1; (4) LP-BM5-infected mice injected with saline; (5) LP-BM5-infected mice injected with control peptide (MCG3); and (6) LP-BM5-infected mice injected with TCR Vβ CDR1 peptide. Group A was comprised of the three uninfected groups, and group B was comprised of the groups infected with LP-BM5.

Administration of peptides (200 μg/mice in saline, i.p.) was performed twice, on days −7 and −3 before retrovirus infection. After 42 days of retrovirus infection, the mice were sacrificed for immunologic analysis. In other experiments, the peptides and saline were injected on days 10 and 14 postinfection. In the dose-response experiment, mice were immunized with different doses of TCR Vβ peptide (0, 5, 25, 100, 200, and 500 μg/mouse, i.p.) on day 10 postinfection. Only in the adjuvant experiment were adjuvants, poly(AU) and Ribi, mixed with the peptide before injection. The mice were sacrificed 14 wk postinfection. The retrovirus was administrated i.p. to mice on 0.1 ml with an ecotrophic (XC) titer of 4.5 $\log_{10}$ PFU/ml, which induces disease with a time course comparable to that previously reported (1). Uninfected normal mice were injected with complete culture medium used for LP-BM5 virus growth as controls. Infection of adult female C57B1/6 mice with LP-BM5 murine leukemia leads to the rapid induction of clinical symptoms with virtually no latent phase.

Peptides

A set of overlapping 16-mer peptides that duplicate the covalent structure of the V$\beta$D$\beta$J$\beta$C$\beta$ protein (15, 16) predicted from a human TCR V$\beta$ gene sequence (17) was produced. TCR V$\beta$ CDR1 that corresponds to the completed CDR1 and N-terminal five residues of Fr2 (15, 18) of the human V$\beta$8.1 gene product (17) has the sequence Cys Lys Pro Ile Ser Gly His Asn Ser Leu Phe Trp Tyr Arg Gln Thr (SEQ ID NO:1). As a control peptide, we used a 16-mer corresponding to the CDR1 of the L chain MCG (19), because the LP-BM5-infected mice did not produce AAb to this peptide. Its sequence is Thr Gly Thr Ser Ser Asp Val Gly Gly Tyr Asn Tyr Val Ser Trp Tyr (SEQ ID NO:2).

The peptide preparations were free of endotoxin. Normal polyclonal IgG pools contain natural AAb against peptide segments corresponding to CDR1, Fr3, and a constant region loop peptide of the TCR $\beta$-chain (15). Unimmunized mice also have natural IgG Ab directed against the same peptide segments; in particular, there is strong reactivity to the human CDR1 test peptides. A computer comparison of human and murine V$\beta$ sequences (S. F. Schulter and J. J. Marchalonis, unpublished analysis) using the progressive alignment algorithm of Feng and Doolittle (20) showed that certain human and murine V$\beta$ sequences could be grouped into families, e.g., human V$\beta$6 and V$\beta$8 correspond to murine V$\beta$11 with human and murine V$\beta$5 in the same clusters.

Standard cytokines and their antibodies

Rat anti-murine IFN-$\gamma$ mAb, standard rIFN-$\gamma$, hamster anti-TNF-$\alpha$ mAb, standard rTNF-$\alpha$, rabbit anti-murine TNF-$\alpha$ serum, rat anti-murine IL-6 mAb, and murine IL-6 were obtained from Genzyme (Boston, Mass.). Rat anti-murine IL-5 and IL-10 Ab, biotin-rat anti-murine IL-5 and IL-10 mAb, and murine rIL-5 and rIL-10 were obtained from Pharmingen (San Diego, Calif.). Goat anti-murine IL-6 polyclonal Ab was obtained from R&D System (Minneapolis Minn.). Rabbit anti-murine IFN-$\gamma$ antiserum was prepared in our laboratory.

ELISA for AAb to TCR-$\beta$ and MCG3

The specific titers of serum IgG to TCR-$\beta$ and MCG3 were determined by ELISA as previously described (15, 16, 18, 19). Briefly, peptides were dissolved in carbonate buffer, pH 9.6 at 1 $\mu$g/well onto Nunc Maxisorb (Nunc. Roskilde, Denmark) 96-well microtiter plates and dried down at 37° C. overnight. The plates were washed with PBST (PBS and 0.05% Tween 20). Nonspecific binding was blocked by incubation with PBSTFG (PBST plus 1.0% fish gelatin). PBSTFG was used as diluent for all sera and conjugated Ab. The plates were washed three times with PBST and incubated for 1.5 h with diluted serum. The plates were washed three times and incubated with horseradish peroxidase-conjugated goat anti-mouse IgG H and L chains (Jackson Immunoresearch, West Grove, Pa.) at a dilution of 1/2000 for 1 h at room temperature. To detect the presence of serum IgG bound to peptide-coated wells, plates were washed three times with PBST and developed with ABTS (Sigma Chemical Co., St. Louis, Mo.) in 0.1 M citrate buffer, pH 4.0. The absorbance at 405 nm was measured after 1 h with a Titertek Multiskan Plus ELISA plate reader EFLABor by Lab Systems and Flow Labs, Finland. Serial twofold dilutions were made for each serum in duplicate with a standard dilution of 1/200. Background binding was measured as the binding of each serum to PBSTFG-blocked microtiter wells in the absence of Ag. The results are represented as the mean titer for each treatment group. The titer for each individual serum was calculated as the inverse dilution at which an absorbance of 0.25 at 405 nm was measured. To allow statistical analysis, a numeric value was required to represent sera that had an absorbance of less than 0.25 at the initial dilution of 1/200. Therefore, sera with no detectable titer were assigned a value of 25, since in our assay, at a dilution of 1/25 most of the sera would have an absorbance close to 0.25. The analysis of variance was conducted using the cell means model: $y_{ijk}$=mean$_{ij}$+$e_{ijk}$, where $y_{ijk}$ is the response for the $k^{th}$ individual who received the $j^{th}$ infection and the $i^{th}$ treatment, means $_{ij}$ is the means response for the $ij^{th}$ group, and $e_{ijk}$ are the random errors associated with the $ijk^{th}$ individual. The e values are assumed to be independent of one another and, given retrovirus status, to have the same variance. For purposes of statistical inference, the e values are also assumed to be normally distributed. The test we used is based on the usual two-sample t-static, but adjusts the degrees of freedom according to the minimum of the sample sizes involved. An adjustment involving bootstrapping the residual errors was made to resolve the issue of multiple comparisons.

ELISA for cytokines

IL-2, IFN-$\gamma$, IL-5, and IL-10 were produced by splenocytes as described previously (21). Briefly, spleens were gently teased with forceps in culture medium (RPMI 1640 containing 10% fetal calf serum, 2mM glutamine, and 100 U/ml penicillin and streptomycin), producing a single cell suspension of spleen cells. Red blood cells were lysed by the addition of a lysis buffer (0.16 M ammonia chloride Tris buffer, pH 7.2) at 37° C. for 2 min. Then, the cells were washed twice with culture medium (CM). The cell concentration was counted and adjusted to 1×10 cells/ml. Splenocyte viability was more than 95%, as determined by trypan blue exclusion. Splenocytes (0.1 ml/well; 1×10$^7$/ml) were cultured in triplicate on 96-well flat bottom culture plates (Falcon, Lincoln Park, N.J.) with CM. Splenocytes were then stimulated with 10 $\mu$g/ml concanavalin A (Con A) (0.1 ml/well: Sigma Chemical Co.) for induction of IL-2 and IL-10 with 24-h incubation and for induction of IL-5 and IFN-$\gamma$ with 72-h incubation at 37° C. in a 5% $CO_2$ incubator. Splenocytes were also stimulated by lipopolysaccharide (LPS, 5 $\mu$g/ml: Life Technologies, Grand Island, N.Y.) for 24 h to induce IL-6 and TNF-$\alpha$ production.

After incubation, the plates were centrifuged for 10 min at 800×g. Supernatant fluids were collected and stored at −70° C. until analysis. They were determined by sandwich ELISA as described previously (21).

Mitogenesis of splenocytes

Splenic T and B cell proliferation was determined by [$^3$H]-thymidine incorporation as described previously (21). Briefly, splenocytes in 0.1 ml of CM (1×10$^7$/ml) were cultured in 96-well flat bottom culture plates (Falcon) with Con A and LPS (5 $\mu$g/ml) and CM. They were incubated at 37° C. in a 5% $CO_2$ incubator for 20 h for Con A-induced T-cell proliferation and for 44 h for LPS-induced B cell proliferation, and then pulsed with [$^3$H]-thymidine (0.5 $\mu$Ci/well: New England Nuclear, Boston, Mass.).

After 4 h, they were harvested by a cell sample harvester (Cambridge Technology, Cambridge, Mass.). Radioactivity was determined by a liquid scintillation counter (Tri-Carb, 2200CA, Packard, Laguna Hills, Calif.). Data are presented as counts per min.

Natural Killer (NK) cell cytotoxicity

NK cell function was measured by a fluorescent concentration release assay modified from the method of Wierda et al. (22) Briefly, this method measures the fluorescent dye 2,7'-bis-(carboxyethyl)5,6'-carboxyfluorescein (Molecular Probes, Eugene, Oreg.,) remaining in the target cells using the Pandex Fluorescence Concentration Analyzer (IDEX, Portland, Me.). YAC-1 target cells were washed once with PBS and labeled with the carboxyfluorescein derivative. Effector to target (E:T) ratios were adjusted to 100:1 and 50:1, and cells were plated in U-bottom microtiter plates (Falcon 3077, Becton Dickinson, Rutherford, N.J.) containing $4 \times 10^4$ target cells/100 µl. The plate was centrifuged (90×g) for 3 min to facilitate cell to cell interaction. The cells were then incubated at 37° C. in a humidified atmosphere of 5% $CO_2$ for 3 h.

After incubation, 20 µl of 1% inert fluoricon polystyrene assay particles were added to each well of the plate (Pandex Harvesting Plate, IDEXX Research Products Div., Westbrook, Me.), and an 80-µl aliquot from each well of the irradiation plate was transferred to a Pantex plate. The epifluorescence of each well in the harvest plate was
automatically read at 485/533 nm excitation/emission wavelengths for 2,7'-bis-(carboxyethyl) 5,6'-carboxyfluorescein using the Pandex Fluorescence Concentration Analyzer. Specific cytotoxicity (percentage) was calculated as follows:

$$\frac{\text{Spontaneous Release} - \text{Experimental Fluorescence}}{\text{Spontaneous Release} - \text{Maximum Release}} \times 100$$

ELISA for IgG detection

Splenocytes ($1 \times 10^7$/ml) from mice in the same experimental group were individually cultured with CM in triplicate on 96-well tissue culture plates (0.1 ml/well; Falcon). Then, splenocytes were stimulated with LPS (Life Technologies; 10 µg/ml, 0.1 ml/well) diluted in CM. After 72-h incubation at 37° C. in a 5% $CO_2$ incubator, the plates were centrifuged for 10 min at 800×g, and supernatant fluids were collected and stored at −70° C. until analysis. Murine IgG production was determined by sandwich ELISA as described previously (21).

Lymphocyte subpopulation measurement of IL-2R+ cells

Mouse spleens were individually collected in complete RPMI 1640 medium, and mononuclear cells were obtained by gently teasing with tweezers. Cell suspensions were washed with medium, and red blood cells (RBC) were lysed in an ammonium chloride solution. The remaining cell suspensions were washed once with cold medium and counted with cosin Y to prepare the desired viable cell concentrations (1–2 million/0.1-ml tube) for lymphocyte surface marker determinations. The numbers of cells expressing IL-2R were determined using rat IgG2a mAb (clone AMT-13) obtained from Boehringer Mannheim (Indianapolis, Ind.) as described previously (23).

Statistics

All parameters were compared between all groups using one-way ANOVA followed by Duncan's multiple range test between any two groups. $p<0.05$ was considered a significant difference between two groups.

Results

Production of AAb to TCR-β and MCG3

Comparison of mean titers of Ab binding TCR Vβ CDR1 peptide (group A—uninfected vs. group B—infected with LP-BM5) indicates that retrovirus infection of C57BL/6 female mice results in a highly significant increase ($p<0.0005$) in specific Ab titers in contrast to that in medium-injected controls. This phenomenon has been regularly observed, and the anti-TCR Ab profile following LP-BM5 infection has been previously characterized. Treatment of retrovirally infected mice with the TCR Vβ CDR1 peptide did not result in a significant increase in mean Ab titers compared with either retrovirally infected, saline-treated mice ($p=0.17$) or retrovirally infected, control peptide-treated mice ($p=0.07$). When sample size is considered, the mean Ab titers of the retrovirally injected TCR Vβ CDR1 peptide-treated group and the retrovirally injected, control peptide-treated group are marginally different. ELISA binding assays did not detect any positive titers to the MCG3 peptide or to blank (background) plates.

Cytokine production

In vitro production of Th1 cytokines, IL-2 and IFN-γ, by Con A-stimulated splenocytes was significantly ($p<0.05$) inhibited in the retrovirus-infected mice. A TCR Vβ peptide was selected because high levels of AAb were induced by the retroviral infection (24, 25). TCR Vβ administration before infection significantly ($p<0.05$) normalized IL-2 and IFN-γ release by Con A-stimulated splenocytes, while administration of the control peptide, MCG3 did not. Release of Th2 cytokines, IL-5 and IL-10, was significantly ($p<0.05$) increased in retrovirus-infected mice. TCR Vβ administration before infection significantly reduced IL-5 and IL-10 release by Con A-stimulated splenocytes, while administration of the control peptide MCG3 did not. Production of TNF-α by LPS-stimulated splenocytes was elevated in the retrovirus-infected mice. TCR Vβ administration significantly ($p<0.05$) inhibited TNF-α release.

TABLE 1

Mean ELISA titers against the target TCR Vβ CDR1 peptide

| Treatment Groups | N | Mean | Min/Max | S.D. |
| --- | --- | --- | --- | --- |
| Group A (total uninfected) | 20 | 326 | 25/1150 | 375 |
| Medium + saline | 8 | 418 | 25/1150 | 447 |
| Medium + MCG3 | 4 | 443 | 25/1150 | 795 |
| Medium + TCR | 8 | 175 | 25/500 | 182 |
| Group B (total infected) | 24 | 1398 | 25/4500 | 1135 |
| LP-BM5 + saline | 8 | 1197 | 25/2800 | 1156 |
| LP-BMT + MCG3 | 8 | 921 | 25/1800 | 597 |
| LP-BM5 + TCR | 8 | 2075 | 25/4500 | 1308 |

Individual sera were screened by ELISA for binding to each antigen with a starting dilution of 1:2000 followed by serial twofold dilutions. A titer of 25 was assigned to any serum with an undetectable titer in order to allow statistical analysis of mean values.

Immune responses

NK cell activity and T and B cell proliferation in response to mitogens were significantly ($p<0.05$) suppressed in the retrovirus-infected mice. TCR Vβ peptide administration before infection significantly ($p<0.05$) normalized the suppressed NK cell activity and 7 cell proliferation, while administration before infection of the control peptide MCG3 did not. TCR Vβ peptide administration before infection prevented the retrovirus-induced suppression of B cell proliferation, but this was not statistically significant.

Murine AIDS symptoms

Hypergammaglobulin production is an important indicator of early retrovirus infection during the progression to murine AIDS. IgG production by LPS-stimulated splenocytes was significantly ($p<0.05$) increased in the retrovirus-infected mice. TCR Vβ administration before infection significantly ($p<0.05$) reduced IgG production, while administration of the control peptide MCG3 did not. Mice were injected with saline, the control peptide (MCG3), or Vβ 8.1 2 and 6 wk post-LP-BM5 infection.

Dose response and adjuvant stimulation

As others found that TCR peptide immunization with high and low doses was less effective at preventing immune dysfunction in autoimmune disease (26), we investigated the actions of different doses of the TCR Vβ peptide on immune dysfunction. The effects of different doses of peptide injected after retrovirus infection on B and T cell mitogenesis in vitro were determined. Doses of 5, 25, and 100 μg/mouse of Vβ peptide prevented only some loss of B cell mitogenesis and did not prevent loss of T cell mitogenesis 16 wk after retrovirus infection when murine AIDS had developed. However, the higher doses (200 μg/mouse, used in all other experiments, as well as 500 μg/mouse) increased both B and T cell mitogenesis. Adjuvants might enhance the effectiveness of Vβ peptide doses that were too low to prevent immune dysfunction. When the TCR Vβ peptide was injected with either of two adjuvants, poly(a)U or Ribi, B cell proliferation in vitro was higher than that in mice injected with the peptide only or saline. T cell mitogenesis was similarly affected at 16 wk of retrovirus infection when murine AIDS had appeared in untreated infected mice.

Immunomodulation in mice immunized with TCR peptide after retrovirus infection

As Vβ peptide immunization postinfection would indicate whether the peptide treatment was normalizing immune dysfunction or preventing its development, mice were immunized at various times postinfection. Injection of the TCR Vβ peptide after retrovirus infection largely prevented the loss of Th1 cytokines, IL-2 and IFN-γ, produced by splenocytes stimulated in vitro with mitogens. Th2 cells were significantly prevented from developing their increased output of the cytokines, IL-5 and IL-6, by TCR Vβ, but not control peptide, immunization performed after retrovirus infection. Immunization after retrovirus inoculation also prevented the loss of T and B cell mitogenesis and the decline in NK cell activity, and somewhat prevented an increase in activated T cells, IL-2R+. Injection of the Vβ peptide after infection also prevented elevation of monocyte cytokine production of IL-6 and TNF as well as IgG synthesis in vitro. However, it did not significantly reduce spleen size. Immunization with the Vβ peptide at increasingly longer times postinfection than 2 wk prevented less of the loss of B cell mitogenesis in vitro.

EXAMPLE 2

Animals and Murine AIDS

Female C57BL/6 mice, 4-weeks old, were obtained from Charles River Laboratories Inc. (Wilmington, Del.). Animals were cared for as required by the University of Arizona Committee on Animal Research. After 2 weeks housing in the animal facility in the Arizona Health Science Center (Tucson, Ariz.), they were randomly assigned to one of the following treatments with 8 mice per group for study A: (1) uninfected, normal mice; (2) uninfected, normal mice injected with saline (pyrogen free); (3) LP-BM5-infected mice injected with 5 μg TCR Vβ CDRI peptide; (4) LP-BM5infected mice injected with 25 μg TCR Vβ CDR1 peptide; (5) LP-BM5 infected mice injected with 100 μg TCR Vβ CDR1 peptide; (6) LP-BM5-infected mice injected with 200 μg TCR Vβ CDR1 peptide; (7) LP-BM5-infected mice injected with 500 μg TCR Vβ CDR1 peptide; (8) LP-BM5-infected mice injected with saline and 200 μg Poly AU adjuvant; (9) LP-BM5-infected mice injected with 25 μg TCR Vβ CDR1 peptide and 230 μg Poly AU adjuvant; (10) LP-BM5-infected mice injected with saline and 230 μg Ribi MPL TDM CWS adjuvant; (11) LP-BM5-infected mice injected with 5 μg TCR Vβ CDR1 peptide and 230 μg Ribi MPL TDM CWS adjuvant; and (12) LP-BM5-infected mice injected with 25 μg TCR Vβ CDR1 peptide and 230 Ribi MPL TDM CWS adjuvant.

LP-BM5 retrovirus was administered intraparitoneally to mice in 0.1 ml saline with an exotropic titre (XC) of 4.5 $\log_{10}$ plaque-forming units (PFU)/ml, which induces disease with a time course comparable to that previously published (1). Administration of peptides (dissolved in saline) and adjuvants were performed 2 weeks after LP-BM5 infection. Uninfected, normal mice were injected with complete culture medium used for LP-BM5 virus growth as controls. Infection of adult female C57BL/6 mice with LP-BM5 MuLV leads to the rapid induction of clinical symptoms with virtually no latent phase.

For study B, the treatment groups were: (1) LP-BM5-infected mice injected with saline 2 weeks after infection; (2) LP-BM5-infected mice injected with 200 μg TCR Vβ CDR1 peptide 2 weeks after infection; (3) LP-BM5-infected mice injected with 200 μg TCR Vβ CDR1 peptide 4 weeks after infection; (4) LP-BM5-infected mice injected with 200 μg TCR Vβ CDR1 peptide 6 weeks after infection; (5) LP-BM5-infected mice injected with 200 μg TCR Vβ CDR1 peptide 8 weeks after infection; and (6) LP-BM5-infected mice injected with 200 μg TCR Vβ CDR1 peptide 10 weeks after infection.

Peptides

A set of overlapping 16-mer peptides that duplicate the covalent structure of the VβDβJβCβ protein (15, 35) predicted from a human TCR Vβ gene sequence (17) was produced. TCR Vβ CDR1 that corresponds to the completed CDR1 and N-terminal five residues of Fr2 (15, 18) of the human Vβ8.1 gene product (17) has the sequence Cys Lys Pro Ile Ser Gly His Asn Ser Leu Phe Trp Tyr Arg Gln Thr (SEQ ID NO:1). Normal polyclonal IgG pools contain natural AAb against peptide segments corresponding to CDR1, Fr3, and a constant region loop peptide of the TCR β-chain (15). Unimmunized mice also have natural IgG Ab directed against the same peptide segments; in particular, there is strong reactivity to the human CDR1 test peptides. A computer comparison of human and murine Vβ sequences (S. F. Schulter and J. J. Marchalonis, unpublished analysis) using the progressive alignment algorithm of Feng and Doolittle (20) showed that certain human and murine VP sequences could be grouped into families, e.g., human Vβ6 and Vβ8 correspond to murine Vβ11 with human and murine Vβ5 in the same clusters.

Standard Cytokines

Rat anti-murine IFN-γ, IL-2-, IL-6-, IL-10-purified antibodies, rat anti-murine IFN-γ, L-2-, IL-6-, IL-10-biotinulated antibodies, and recombinant murine IFN-γ, IL-2-, IL-6-, IL-10 were obtained from Pharmingen (San Diego, Calif.).

ELISA for cytokines

IL-2, IFN-γ, IL-6, and IL- 10 were produced by splenocytes as described previously (21). Briefly, spleens were gently teased with forceps in culture medium (RPMI 1640 containing 10% fetal calf serum, 2mM glutamine, and 100 U/ml penicillin and streptomycin), producing a single cell suspension of spleen cells. Red blood cells were lysed by the addition of a lysis buffer (0.16 M ammonia chloride Tris buffer, pH 7.2) at 37° C. for 3 min. Then, the cells were washed twice with culture medium (CM). The cell concentration was counted and adjusted to $1\times10^7$ cells/ml. Splenocyte viability was more than 95%, as determined by trypan blue exclusion. Splenocytes (0.1 ml/well; $1\times10^7$/ml)

were cultured in triplicate on 96-well flat bottom culture plates (Falcon, Lincoln Park, N.J.) with CM. Splenocytes were then stimulated with 10 μg/ml concanavalin A (Con A) (0.1 ml/well: Sigma Chemical Co.) for induction of IL-2 and IL-10 with 24-h incubation and for induction of IL-5 and IFN-γ with 72-h incubation at 37° C. in a 5% $CO_2$ incubator. Splenocytes were also stimulated by lipopolysaccharide (LPS, 10 μg/ml: Gibco, Grand Island, N.Y.) for 24 h to induce IL-6 production. After incubation, the plates were centrifuged for 10 min at 800×g. Supernatant fluids were collected and stored at −70° C. until analysis. They were determined by sandwich ELISA as described previously (21).

Mitogenesis of splenocytes

Splenic T and B cell proliferation was determined by [$^3$H]-thymidine incorporation as described previously (21). Briefly, splenocytes in 0.1 ml of CM ($1 \times 10^7$/ml) were cultured in 96-well flat bottom culture plates (Falcon) with Con A and LPS (10 μg/ml). They were incubated at 37° C. in a 5% $CO_2$ incubator for 20 h for Con A-induced T-cell proliferation and for 44 h for LPS-induced B cell proliferation, and then pulsed with [$^3$H]-thymidine (0.5 μCi/well: New England Nuclear, Boston, Mass.). After 4 h, they were harvested by a cell sample harvester (Cambridge Technology, Cambridge, Mass.). Radioactivity was determined by a liquid scintillation counter (Tri-Carb, 2200CA, Packard, Laguna Hills, Calif.). Data was presented as counts per minute.

Natural Killer (NK) cell cytotoxicity

NK cell function was measured by a fluorescent concentration release assay modified from the method of Wierda et al. (22) Briefly, this method measures the fluorescent dye 2,7'-bis-(carboxyethyl)5,6'-carboxyfluorescein (Molecular Probes, Eugene, Oreg.) remaining in the target cells using the Pandex Fluorescence Concentration Analyzer (IDEX, Portland, Me.). YAC-1 target cells were washed once with PBS and labeled with the carboxyfluorescein derivative. Effector to target (E:T) ratios were adjusted to 100:1 and 50:1, and cells were plated in U-bottom microtiter plates (Falcon 3077, Becton Dickinson, Rutherford, N.J.) containing $4 \times 10^4$ target cells/100 μl. The plate was centrifuged (90×g) for 3 min to facilitate cell to cell interaction. The cells were then incubated at 37° C. in a humidified atmosphere of 5% $CO_2$ for 3 h. After incubation, 20 μl of 1% inert fluoricon polystyrene assay particles were added to each well of the plate (Pandex Harvesting Plate, IDEXX Research Products Div., Westbrook, Me.), and an 80-μl aliquot from each well of the irradiation plate was transferred to a Pantex plate. The epifluorescence of each well in the harvest plate was automatically read at 485/533 nm excitation/emission wavelengths for 2,7'-bis-(carboxyethyl) 5,6'-carboxyfluorescein using the Pandex Fluorescence Concentration Analyzer. Specific cytotoxicity (percentage) was calculated as follows:

$$\frac{\text{Spontaneous Release} - \text{Experimental Fluorescence}}{\text{Spontaneous Release} - \text{Maximum Release}} \times 100$$

Statistics

The statistic tests for comparison among groups were finished in NCSS program (Kaysville, Utah) using Friedman's Block/Treatmnent test, followed by Duncan's Multiple Range Test between any two groups. P<0.05 was considered a significant difference between two groups.

Results

Body weight

There was no change in food consumption because of infection or injection. The body weight of the mice was not affected by various levels of TCR Vβ CDR1 peptide injection or time course of injection postinfection. The spleen and lymph node weights were significantly (P<0.05) elevated in the infected mice, which indicated that infection had progressed to murine AIDS.

Mitogenesis of splenocytes

Proliferation of Con-A and LPS-induced splenocytes was significantly decreased (P<0.05) by murine retrovirus infection. Suppression of T- and B-cell proliferation in the spleen, induced by retrovirus infection, was significantly (P<0.05) prevented by TCR Vβ CDR1 peptide injection. Peptide dosages above 200 μg/mouse and injection before 4 weeks postinfection maintained near normal T- and B-cell proliferation which were significantly (P<0.05) higher than that in infected, unimmunized mice. Injection with less than 200 μg/mouse of peptide or at 6–10 weeks postinfection did not prevent development of decreased, in vitro proliferation of mitogen-stimulated T and B cells.

Nature killer (NK) cell cytotoxicity

Murine retrovirus infection significantly (P<0.05) reduced the splenic NK cell activity, which was largely (P<0.05) maintained in infected mice injected with the TCR Vβ CDR1 peptide. Peptide dosages above 100 μg/mouse and injection by 4 weeks postinfection maintained near-normal NK cell activity which was significantly (P<0.05) higher than that in infected, unimmunized mice. Injection with less than 100 μg/mouse at or after 6-weeks postinfection permitted development of a significantly decreased NK cell cytotoxicity.

Influence of adjuvants on TCR immunization

The adjuvants used generally had no significant (P>0.05) effect on maintaining the immune function.

Cytokine production of splenocytes

In vitro production of Th1 cytokines, IL-2 and IFN-γ by Con A-stimulated splenocytes was significantly (P<0.05) inhibited in the retrovirus-infected mice. TCR Vβ CDR1 peptide injection significantly (P<0.05) normalized IL-2 and IFN-γ release by mitogen-stimulated splenocytes compared with infected, unimmunized mice. Injection with 200 μg/mouse or higher dose of peptide and before 6-weeks postinfection maintained near-normal Th1 cytokine production which were significantly (P<0.05) higher than that in infected, unimmunized mice. Injection at dosages of less than 200 μg/mouse or after 6-weeks postinfection had significantly (P<0.05) decreased Th1 cytokine production.

Release of Th2 cytokines, IL-6 and IL-10 in vitro by mitogen-stimulated spleen cells, was significantly (P<0.05) increased in the retrovirus-infected mice. TCR Vβ CDR1 peptide injection significantly (P<0.05) normalized IL-6 and IL-10 release by mitogen-stimulated splenocytes. Immunization with TCR Vβ CDR1 peptide above 100 μg/mouse and 4 weeks postinfection maintained near-normal Th2 cytokine production which was significantly (P<0.05) lower than that of infected, unimmunized mice. Injection at dosages of less than 100 μg/mouse or after 4-weeks postinfection permitted development of a significantly (P<0.05) increased Th2 cytokine production.

Those skilled in the art will recognize that, while specific embodiments have been illustrated and described, various modifications and changes may be made without departing from the spirit and scope of the invention.

REFERENCES

The following references, to the extent that they provide exemplary procedural or other details supplementary to those set forth herein, are specifically incorporated herein by reference.

1. Watson, R. R. 1989, Minireview of murine models for acquired immune deficiency syndrome. *Life Sci*, 44:iii.
2. Fauci, A. S. 1993, Multifactorial nature of human immunodeficiency virus disease: implications for therapy, *Science* 262:1011.
3. Selvey, L. A., H. C. Mose III, L. G. Graner, and R. J. Hodes, 1993. Preferential expansion and activation of Vβ5+ CD4+ T cells in murine acquired immunodeficiency syndrome. *J. Immunol.* 151:1712.
4. Soudeyns, H. N. Rebai, G. P. Pantaleo, C. Ciruli, T. Boghossian, P. P. Sekaly, and A. S. Fauci, 1993. The T cell receptor V beta repertoire in HIV-1 infection and disease, *Semin. Immunol.* 5:175.
5. Imberti, L., A. Sottini, A. Bettinaridi, M. Puoti, and D. Primi, 1991. Selective depletion in HIV infection of T cells that bear specific T cell receptor Vβ sequences. *Science* 254:860.
6. Clerici, M., and G. M. Shearer, 1993. A $T_H1 \rightarrow T_H2$ switch is a critical step in the etiology of HIV infection. *Immunol. Today* 14:107.
7. Bradley, W. G., N. Ogata, R. A. Good, and N. K. Day, 1993. Alteration of in vivo cytokine gene expression in mice infected with a molecular clone the defective MAIDS virus. *J. AIDS* 7:1.
8. Sher, A., R. T. Gazzinelli, I. P. Oswald, M. Clerici, M. Kullberg, E. J. Pearce, J. A. Berzofsky, T. R. Mosmann, S. L. James, H. C. Morse III, and G. M. Shearer, 1992. Role of T-cell derived cytokines in the downregulation of immune responses in parasitic and retroviral infection. *Immunol. Rev.* 127:183.
9. Wang, Y., D. S. Huang, P. T. Giger, and R. R. Watson, 1993. The kinetics of imbalanced cytokine production by T cells and macrophages during the murine AIDS, *Adv. Biosci.* 86:335.
10. Gazzinelli, R. T., M. Makino, S. K. Chattopadhyay, C. M. Sanpper, A. Sher, A. W. Hugin, and H. C. Morse III, 1992. Preferential activation of Th2 cells during progression of retrovirus-induced immunodeficiency in mice. *J. Immunol.* 148:182.
11. Kanagawa, O., B. A. Vaupel, S. Gayama, G. Koehler, and M. Kopf, 1993. Resistance of mice deficient in IL-4 to retrovirus-induced immunodeficiency syndrome (MAIDS). *Science* 262:240.
12. Wang, Y., S. K. Ardestain, B. Liang, L. Beckham, and R. R. Watson, 1994. Anti-IL-4 monoclonal antibody and interferon-γ administration retards development of immune dysfunction and cytokine dysregulation during murine AIDS. *Immunology* 83:384.
13. Marchalonis, J. J., K. Deghanpisheh, D. Huang, S. F. Schluter, and R. R. Watson, 1994. Autoantibodies to T-cell receptors following infection by murine retrovirus. *Lymphology* 27S:853.
14. Victor-Korbin, C., F. A. Bonilla, Z. Barak, and C. Bona, 1989. Structural correlates of a regulatory idiotype. *Immunol. Rev.* I110:151.
15. Marchalonis, J. J., H. Kaymaza, F. Dedoglu, S. F. Schluter, D. E. Yocum, and A. B. Edmundson, 1992. Human autoantibodies reactive with synthetic autoantigens from β-cell receptor β chain. *Proc. Natl. Acad. Sci. USA* 89:332.
16. Dedeoglu, F., R. A. Hubbard, S. F. Schluter, and J. J. Marchalonis, 1991. T-Cell receptors of man and mouse studied with antibodies against synthetic peptides. *Exp. Clin. Immunogenet*, 9:95.
17. Toyonaga, B., and T. W. Mak, 1987. Genes of the T-cell antigen receptor in normal and malignant T-cells. *Annu. Rev. Immunol.* 5:585.
18. Kaymaz, H., F. Dedeoglu, S. F. Schluter, A. B. Edmundson, and J. J. Marchalonis, 1993. Reactions of anti-immunoglobulin sera with synthetic T-cell receptor peptides: implications for the three-dimensional structure and function of the TCRβ chain. *Int. Immunol.* 5:941.
19. Marchalonis, J. J., H. Kaymaz, F. Dedeoglu, S. F. Schluter, and A. B. Edmundson, 1992. Antigenic mapping of a human light chain: correlation with 3-dimensional structure. *J Protein Chem.* 11: 129.
20. Feng, D. F., and R. F. Doolittle, 1987. Progressive sequence alignment as a prerequisite to correct phylogenetic trees. *J. Mol. Evol.* 25:351.
21. Wang, Y., D. S. Huang, P. T. Giger, and R. R. Watson, 1994. Influence of chronic dietary ethanol on cytokine production by murine splenocytes and thymocytes. *Alcohol. Clin. Exp. Res.* 18:8.
22. Wierda, W. G., D. S. Mehr, and Y. B. Kim, 1989. Comparison of fluorochrome-labeled and $^{51}$Cr-labeled targets for natural killer cytotoxicity assay. *J Immunol. Methods* 122:15.
23. Watson, R. R., O. E. Odeleye, H. R. Darban, and M. C. Lopez, 1992. Modification of lymphoid subsets by chronic ethanol consumption in C57BL/6 mice infected with LP-BM5 murine leukemia virus. *Alcohol Alcoholism* 27:417.
24. Dehghanpisheh, K., D. S. Huang, S. F. Schuter, R. R. Watson, and J. J. Marchalonis, 1995. Production of IGG autoantibodies to T-cell receptors in mice infected with the retrovirus LP-BM5, Int. Immunol. 7:31.
25. Lake, D. F., S. F. Schluter, E. Wang, R. M. Bernstein, A. B. Edmundson, and J. J. Marchalonis, 1994. Autoantibodies to the alpha/beta T-cell receptors in human immunodeficiency virus (HIV) infection: dysregulation and mimicry. *Proc. Natl. Acad. Sci. USA* 91:10849.
26. Boardette, D. N., R. H. Whitman, Y. K. Chou, W. J. Morrison, J. Atherton, C. Kenny, D. Liefeld, G. A. Hashim, H. Offner, and A. A. Vandenbark, 1994. Immunity to TCR peptides in multiple sclerosis, I. Successful immunization of patients with synthetic Vβ 5.1 and Vβ 6.1 CDR2 peptides. *J. Immunol.* 152:2510.
27. Doherty, T. M., H. C. Morse III, and R. L. Coffman, 1995. Modulation of specific T cell responses by concurrent infection with *Leishmania major* and LP-BM5 murine leukemia viruses. *Int. Immunol.* 7:131.
28. Odeleye, O. E., C. D. Eskelson, and R. R. Watson, 1992, Changes in hepatic lipid composition after infection by LP-BM5 causing murine AIDS. *Life Sci.* 51:129.
29. Wang, Y., B. Liang, and R. R. Watson, 1994. Suppression of tissue levels of vitamin A, E, zinc and copper in murine AIDS. *Nutr. Res.* 14:1031.
30. Mellors, J. W., B. P. Griffith, M. A. Ortiz, M. L. Landry, and J. L. Ryan, 1991. Tumor necrosis factor-alpha/cachectin enhances human immunodeficiency virus type 1 replication in primary macrophages. *J Infect. Dis.* 163:78.
31. Pantaloo, G., J. F. Demarest, H. Soudeyns, C. Graziosi, F. Denis, J. W. Adelsberger, P. Borrow, M. S. Saag, G. M. Shaw, R. P. Sekaly, and A. S. Fauci, 1994. Major expansion of CD8+ T cells with predominant VB usage during the primary immune response to HIV. *Nature* 370:463.
32. Marchalonis, J. J., D. F. Lake, S. F. Schluter, K. Dehghanpisheh, R. R. Watson, N. M. Ampel, and J. N. Galgiani, 1995. Autoantibodies against peptide-defined epitopes of T-cell receptors in retrovirally infected humans and mice. In *Proceedings of the VIIIth International Symposium on Immunobiology of Proteins and Peptides*. Plenum Press, New York, in press.

33. Nabozny, G. H., M. I. Bull, J. Hanson, M. M. Griffiths, H. S. Luthra, and C. S. David, 1994. Collagen-induced arthritis in T cell receptor Vβ cogenic B10.Q mice. *J Exp. Med.* 180:517.
34. Liang, B., J. J. Marchalonis, Z. Zhang,, and R. R. Watson, 1996. Effects of vaccination against different T-cell receptors on maintenance of immune function during murine retrovirus infection. *Cell. Immunol.*, in press.
35. Marchalonis, J. J., S. F. Schluter, E. Wang, et al., 1994. Synthetic autoantigens of immunoglobulins and T-cell receptors: their recognition in aging, infection and autoimmunity. *Proc. Soc. Expt. Biol.* 207, 129.
36. Liang, B., S. Ardestani, H. Chow, C. Eskelson & R. R. Watson, 1996. Prevention of vitamin E deficiency during murine retrovirus infection by maintenance of immune function. *J. Nutr.* (in press).
37. Clerici, M., F. T. Hakim, D. J. Venzon et al., 1993. Changes in interleukin-2 and interleukin-4 production in asymptomatic, human immunodeficiency virus-seropositive individuals. *J. Clin. Invest.* 91, 759.
38. Balkwill, F. R. & F. Burke, 1989. The cytokine network. *Immunol Today.* 10, 229.
39. Boue, F., C. Wallon, C. Goujard, F. Barre-Sinoussi, P. Galanaud & J. F. Delfraissy, 1992. HIV induced IL-6 production by human B lymphocytes: Role of IL-4. *J Immunol* 148, 3761.
40. Van Snick, J., 1990. Interleukin-6: an overview. *Annu. Rev. Immunol* 8, 253.
41. Poli, G., P. Bressler, A Kinter, et al., 1990. Interleukin-6 induces human immunodeficiency virus expression in infected monocytic cells alone and in synergy with tumor necrosis factor alpha by transcriptional post-transcriptional mechanisms. *J. Exp. Med.* 172, 151.

What is claimed is:

1. A method of modulating the immune response in a mammal infected with a C-type retrovirus or a lentivirus, comprising administering by a systemic route an amount of T-cell receptor Vβ CDR1 peptide of SEQ ID NO:1 sufficient to stimulate the production of interleukin 2 and interferon-γ, and to suppress the production of interleukin 5, interleukin 6, interleukin 10, and immunoglobulin G.

2. The method of claim 1, wherein said lentivirus comprises HIV.

3. A method of altering the immune system response of a host infected with a C-type retrovirus or a lentivirus, comprising artificially introducing a T-cell receptor Vβ CDR1 peptide of SEQ ID NO: 1 into the bloodstream or immune system by injection so as to artificially induce said immune system to stimulate production of Th1 cytokines or suppress production of Th2 derived cytokines.

4. The method of claim 3, wherein said lentivirus comprises HIV.

5. The method of claim 3, wherein said lentivirus comprises feline immunodeficiency virus.

6. A method of altering the immune system response of a host suffering from an infectious disease comprising artificially introducing a T-cell receptor Vβ CDR1 peptide of SEQ ID NO: 1 into the bloodstream or immune system by injection so as to artificially induce said immune system to stimulate production of Th1 cytokines or suppress production of Th2 derived cytokines.

* * * * *